(12) United States Patent
Burkhart et al.

(10) Patent No.: US 10,537,318 B2
(45) Date of Patent: *****Jan. 21, 2020

(54) METHOD FOR KNOTLESS FIXATION OF TISSUE

(71) Applicant: Arthrex, Inc., Naples, FL (US)

(72) Inventors: Stephen S. Burkhart, Boerne, TX (US); R. Donald Grafton, Naples, FL (US); Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 378 days.

This patent is subject to a terminal disclaimer.

(21) Appl. No.: 15/355,600

(22) Filed: Nov. 18, 2016

(65) Prior Publication Data

US 2017/0135689 A1 May 18, 2017

Related U.S. Application Data

(60) Continuation of application No. 14/615,044, filed on Feb. 5, 2015, now abandoned, which is a division of application No. 11/802,057, filed on May 18, 2007, now Pat. No. 9,005,246.

(60) Provisional application No. 60/801,097, filed on May 18, 2006.

(51) Int. Cl.
*A61B 17/04* (2006.01)

(52) U.S. Cl.
CPC .... *A61B 17/0401* (2013.01); *A61B 2017/044* (2013.01); *A61B 2017/045* (2013.01); *A61B 2017/0408* (2013.01); *A61B 2017/0409* (2013.01); *A61B 2017/0412* (2013.01); *A61B 2017/0438* (2013.01); *A61B 2017/0454* (2013.01)

(58) Field of Classification Search
CPC ........ A61B 17/0401; A61B 2017/0409; A61B 2017/0411; A61B 2017/0424; A61B 2017/043; A61B 2017/0432; A61B 2017/0445; A61B 2017/0458

See application file for complete search history.

(56) References Cited

U.S. PATENT DOCUMENTS

| | | |
|---|---|---|
| 4,484,570 A | 11/1984 | Sutter et al. |
| 4,870,957 A | 10/1989 | Goble et al. |
| 5,084,050 A | 1/1992 | Draenert |
| 5,129,904 A | 7/1992 | Illi |
| 5,152,790 A | 10/1992 | Rosenberg et al. |
| 5,249,899 A | 10/1993 | Wilson |
| 5,411,523 A | 5/1995 | Goble |
| 5,423,860 A | 6/1995 | Lizardi et al. |

(Continued)

FOREIGN PATENT DOCUMENTS

| | | |
|---|---|---|
| EP | 1 707 127 A1 | 10/2006 |
| EP | 1707127 A1 * | 10/2006 ......... A61B 17/0401 |

(Continued)

*Primary Examiner* — Christopher L Templeton
(74) *Attorney, Agent, or Firm* — Blank Rome LLP

(57) ABSTRACT

A suture anchor for knotless fixation of tissue. A swivel suture anchor has an anchor tip for receiving a suture strand, for surgical tissue repair without requiring suture knots. Tension on the repair constructs is adjustable. The swivel anchor is secured in a hole in bone by advancing a fixation device, such as a cannulated interference screw, over the body of the anchor.

3 Claims, 10 Drawing Sheets

(56) References Cited

U.S. PATENT DOCUMENTS

| | | |
|---|---|---|
| 5,458,601 A | 10/1995 | Young, Jr. |
| 5,500,000 A | 3/1996 | Feagin et al. |
| 5,540,718 A | 7/1996 | Bartlett |
| 5,545,180 A | 8/1996 | Le et al. |
| 5,702,398 A | 12/1997 | Tarabishy |
| 5,766,250 A | 6/1998 | Chervitz |
| 5,860,973 A | 1/1999 | Michelson |
| 5,957,953 A | 9/1999 | DiPoto |
| 5,968,047 A | 10/1999 | Reed |
| 6,027,523 A | 2/2000 | Schmieding |
| 6,045,574 A | 4/2000 | Thal |
| 6,048,343 A | 4/2000 | Mathis et al. |
| 6,083,522 A | 7/2000 | Chu |
| 6,086,608 A | 7/2000 | Ek |
| 6,143,017 A | 11/2000 | Thal |
| 6,214,007 B1 | 4/2001 | Anderson |
| 6,267,766 B1 | 7/2001 | Burkhart |
| 6,355,043 B1 | 3/2002 | Adam |
| 6,368,326 B1 | 4/2002 | Dakin |
| 6,464,706 B1 | 10/2002 | Winters |
| 6,517,542 B1 | 2/2003 | Papay |
| 6,527,794 B1 | 3/2003 | McDevitt et al. |
| 6,533,816 B2 | 3/2003 | Sklar |
| 6,544,281 B2 | 4/2003 | Elattrache et al. |
| 6,589,245 B1 | 7/2003 | Weiler et al. |
| 6,666,877 B2 | 12/2003 | Morgan |
| 6,840,953 B2 | 1/2005 | Martinek |
| 6,863,671 B1 | 3/2005 | Strobel et al. |
| 6,939,135 B2 | 9/2005 | Sapian |
| 7,083,647 B1 | 8/2006 | Sklar et al. |
| 7,090,690 B2 | 8/2006 | Foerster |
| 7,261,716 B2 | 8/2007 | Strobel et al. |
| 7,300,439 B2 | 11/2007 | May |
| 7,329,272 B2 | 2/2008 | Burkhart et al. |
| 7,491,217 B1 | 2/2009 | Hendren |
| 7,585,311 B2 | 9/2009 | Green et al. |
| 7,588,587 B2 | 9/2009 | Barbieri et al. |
| 7,645,293 B2 | 1/2010 | Martinek et al. |
| 7,717,947 B1 | 5/2010 | Wilberg et al. |
| 7,803,173 B2 | 9/2010 | Burkhart et al. |
| 7,976,565 B1 | 7/2011 | Meridew |
| 7,981,140 B2 | 7/2011 | Burkhart |
| 7,993,369 B2 | 8/2011 | Dreyfuss |
| 8,012,174 B2 | 9/2011 | ElAttrache et al. |
| 8,114,127 B2 | 2/2012 | West, Jr. |
| 8,663,279 B2 | 3/2014 | Burkhart et al. |
| 9,005,246 B2 | 4/2015 | Burkhart et al. |
| 2002/0013608 A1* | 1/2002 | Elattrache .......... A61B 17/0401 606/232 |
| 2002/0052629 A1 | 5/2002 | Morgan |
| 2002/0156476 A1 | 10/2002 | Wilford |
| 2003/0153947 A1 | 8/2003 | Koseki |
| 2004/0093030 A1 | 5/2004 | Cox et al. |
| 2004/0093031 A1* | 5/2004 | Burkhart .......... A61B 17/0401 606/232 |
| 2004/0193217 A1 | 9/2004 | Lubbers et al. |
| 2004/0193285 A1 | 9/2004 | Roller |
| 2004/0225292 A1 | 11/2004 | Sasso et al. |
| 2005/0119698 A1 | 6/2005 | Martinek |
| 2005/0245932 A1 | 11/2005 | Fanton |
| 2006/0004364 A1 | 1/2006 | Green et al. |
| 2006/0079904 A1 | 4/2006 | Thal |
| 2006/0100630 A1 | 5/2006 | West, Jr. |
| 2006/0235413 A1 | 10/2006 | Denham et al. |
| 2006/0247642 A1 | 11/2006 | Stone et al. |
| 2006/0259076 A1* | 11/2006 | Burkhart .......... A61B 17/0401 606/228 |
| 2007/0038221 A1 | 2/2007 | Fine et al. |
| 2007/0060922 A1 | 3/2007 | Dreyfuss |
| 2007/0135843 A1 | 6/2007 | Burkhart |
| 2007/0191849 A1 | 8/2007 | ElAttrache |
| 2007/0225719 A1 | 9/2007 | Stone et al. |
| 2008/0004659 A1 | 1/2008 | Burkhart et al. |
| 2008/0009904 A1 | 1/2008 | Bourque et al. |
| 2008/0154314 A1 | 6/2008 | McDevitt |
| 2008/0208253 A1 | 8/2008 | Dreyfuss et al. |
| 2008/0215091 A1 | 9/2008 | Dreyfuss |
| 2008/0275431 A1 | 11/2008 | Stone et al. |
| 2008/0281325 A1 | 11/2008 | Stone et al. |
| 2008/0288070 A1 | 11/2008 | Lo |
| 2009/0192546 A1 | 7/2009 | Schmieding et al. |
| 2009/0281581 A1 | 11/2009 | Berg |
| 2009/0287259 A1 | 11/2009 | Trenhaile |
| 2010/0248888 A1 | 9/2010 | Hamperl |
| 2010/0249854 A1 | 9/2010 | Thomas |
| 2010/0331896 A1 | 12/2010 | Le Couedic et al. |
| 2011/0106252 A1 | 5/2011 | Barwood |
| 2011/0313455 A1 | 12/2011 | ElAttrache et al. |
| 2012/0022588 A1 | 1/2012 | Berg |
| 2012/0165868 A1 | 6/2012 | Burkhart et al. |
| 2013/0035721 A1 | 2/2013 | Brunelle |
| 2013/0158597 A1 | 6/2013 | Hernandez |
| 2013/0345750 A1 | 12/2013 | Sullivan |
| 2014/0364906 A1 | 12/2014 | Palese |

FOREIGN PATENT DOCUMENTS

| | | |
|---|---|---|
| EP | 1 857 054 A2 | 11/2007 |
| WO | WO 2006/060035 A2 | 6/2006 |
| WO | WO 2006/099109 A2 | 9/2006 |

* cited by examiner

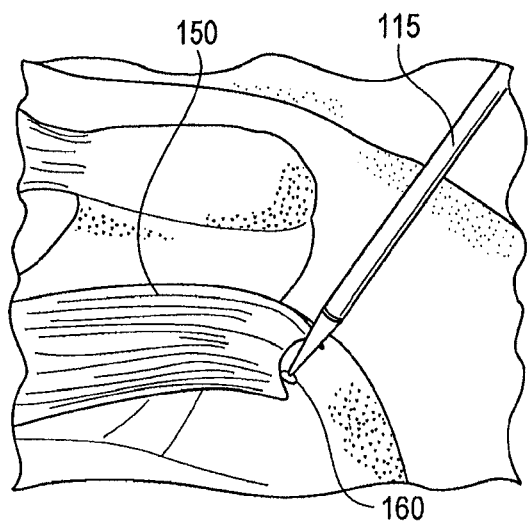
FIG. 9
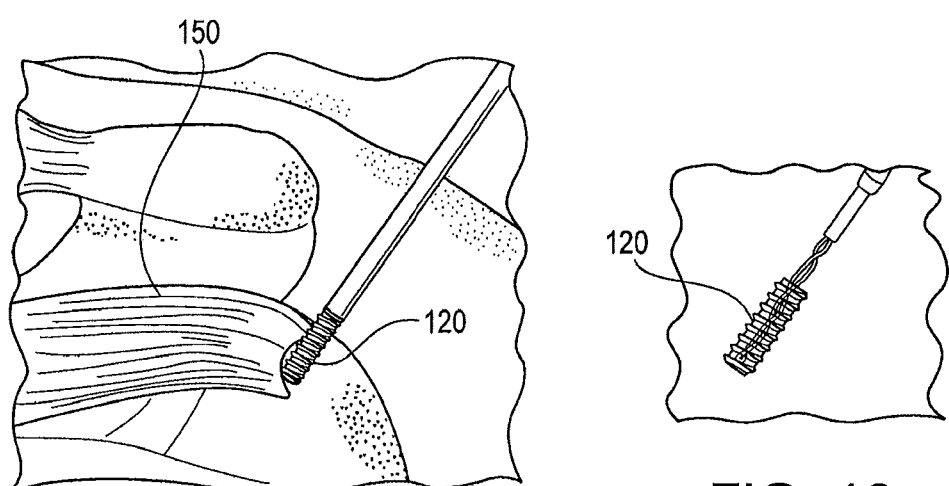
FIG. 10
FIG. 10a

METHOD FOR KNOTLESS FIXATION OF TISSUE

This application is a continuation of application Ser. No. 14/615,044, filed Feb. 5, 2015, which is a divisional of application Ser. No. 11/802,057, filed May 18, 2007, now U.S. Pat. No. 9,005,246, which claims the benefit of U.S. Provisional Application Ser. No. 60/801,097, filed May 18, 2006, the entire disclosures of which are incorporated herein by reference.

BACKGROUND OF THE INVENTION

1. Field of the Invention

The present invention relates to surgical fixation and, more particularly, to methods of conducting anatomical tissue repair, such as ligament repair and reconstruction, using a swivel suture anchor for knotless tissue fixation.

2. Description of the Related Art

Securing suture during surgery can be difficult and demanding. Various suture constructs have been developed in an effort to avoid the need to tie knots in suture, particularly during arthroscopic surgery. For example, U.S. Pat. No. 6,143,017 to Thal discloses tissue fixation using a freestanding continuous suture loop that is snagged by an anchoring device. While it appears that tissue can be bound to bone according to the Thal teachings, it is not evident how to accomplish in situ surgical refinements such as adjustment of the loop length or tension on the repaired tissue. Accordingly, there exists a need in the art for improved technology for knotless tissue fixation.

SUMMARY OF THE INVENTION

The present invention provides apparatus and methods for anatomical tissue repair and reconstruction, using a swivel anchor for knotless tissue fixation. In one method of tissue fixation, the swivel anchor is used with a suture chain formed of at least two loops formed of high strength suture. A driver is provided direct the tip of the swivel anchor to capture loops of the suture chain. The swivel anchor is locked and secured in bone by inserting a cannulated fixation device (for example, an anchor, an interference plug or screw, or an implant) over the anchor.

The present invention also provides a method for knotless fixation of anatomical tissue during surgical applications by employing a swivel anchor assembly and a suture chain. The method comprises the steps of: (i) providing a suture chain formed of at least two loops formed of and connected by suture; (ii) securing an end of the suture chain to a fixation device; (iii) securely engaging a swivel anchor with at least a portion of the fixation device; and (iv) pulling on the other end of the suture chain to tension the suture chain and the tissue coupled thereto.

Other features and advantages of the present invention will become apparent from the following description of exemplary embodiments of the invention described with reference to the accompanying drawings.

BRIEF DESCRIPTION OF THE DRAWINGS

FIGS. 9-16 and 16a depict a series of subsequent steps of shoulder repair using a double-row technique with a swivel anchor device according to the present invention.

DETAILED DESCRIPTION OF THE PREFERRED EMBODIMENTS

Figure 1:
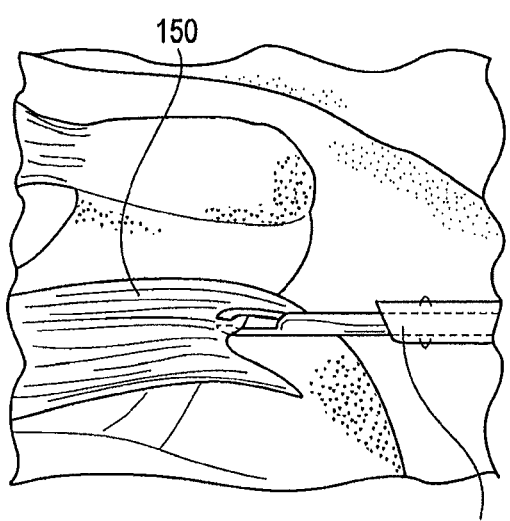
FIGS. 1-8 and 8a depict a series of subsequent steps of shoulder repair using a single-row technique with a swivel anchor device according to the present invention.

The present invention provides apparatus and methods for knotless tissue fixation using a swivel anchor device. In a preferred method, the swivel anchor is used with a suture chain formed of at least two loops of suture, preferably high strength suture. The loops of the chain are captured by mounting the swivel anchor on a driver. The driver is also used to engage and lock the swivel anchor in a hole in bone by inserting a cannulated fixation device (for example, an anchor, an interference plug or screw, or an implant) over the anchor.

The present invention also provides a method for knotless fixation of anatomical tissue during surgical applications by employing a swivel anchor and a suture chain. The method comprises the steps of: (i) providing a suture chain formed of at least two loops formed of and connected by suture; (ii) securing an end of the suture chain to a fixation device; (iii) securely engaging a swivel lock with at least a portion of the fixation device; and (iv) pulling on the other end of the suture chain to tension the suture chain and the soft tissue coupled thereto.

Suture chains used in accordance with the present invention are described in detail in U.S. Application Publication No. 2006/0259076, the entire disclosure of which is incorporated by reference herein. The term "chain" is used in the specification and claims to refer to exemplary embodiments of the invention. A "chain" in this context refers broadly to a suture construct formed of a series of suture loops. The loops can be, but need not be, interlinked. In this manner, the term "chain" as used in this application includes, but need not be limited to, the commonly understood definition in which links or rings are fitted into one another. Rather, the chains of the present invention can include two or more loops that are connected together. Each loop preferably has a fixed perimeter. The suture can be interlaced, rather than knotted, as described further below, to establish and maintain loop geometry. Preferably, all loops are similar in size.

Referring now to the drawings, where like elements are designated by like reference numerals, FIGS. 1-16 and 16a illustrate two surgical procedures of approximating tissue (for example, a torn tendon) to bone according to exemplary embodiments of the present invention. For simplicity, the invention will be described below with reference to fixation of the rotator cuff; however, the invention is not limited to this exemplary embodiment and has applicability to fixation of tissue in general, such as, for example, fixation of torn tendons in ACL reconstructions of the knee or in fixation of any tendon to bone.

Method steps of tissue fixation according to exemplary embodiments of the present invention are depicted schematically in FIGS. 1-16 and 16a. As described in more detail below, FIGS. 1-8 illustrate sequential steps during a rotator cuff repair using a knotless single row technique and FIGS. 9-16 and 16a illustrate sequential steps during a rotator cuff repair using a knotless double row technique. Both techniques will be described with reference to driver assembly 100 (FIGS. 17a-20), swivel lock anchor 200 (FIG. 21) and fixation device 300 (FIG. 22).

Although the single and double row techniques are described below with reference to specific instruments sold by Arthrex, Inc., the assignee of the present application, and with reference to a series of specific steps and devices used during the surgical tissue fixation, it should be understood that the invention is not limited to the specific disclosure of these embodiments and contemplates modifications and variations that are apparent to those skilled in the art. Accordingly, the invention must not be limited to the specific embodiments detailed below, as they are only exemplary in nature.

Knotless Single Row Repair Technique—FIGS. 1-8

FIGS. 1-8 illustrate a series of subsequent steps in shoulder repair for a single-row repair technique using a swivel lock device according to the present invention.

The mobility of the tear is assessed using a suture retriever/tissue grasper 105, such as the Arthrex KingFisher™ Suture Retriever/Tissue Grasper, as shown in FIG. 1. In the case of a large U-shaped tear, margin convergence suturing may be required before approximation. Then, a shaver, high-speed burr, or chondro pick is used to prepare a bleeding bone bed.

Figure 2:
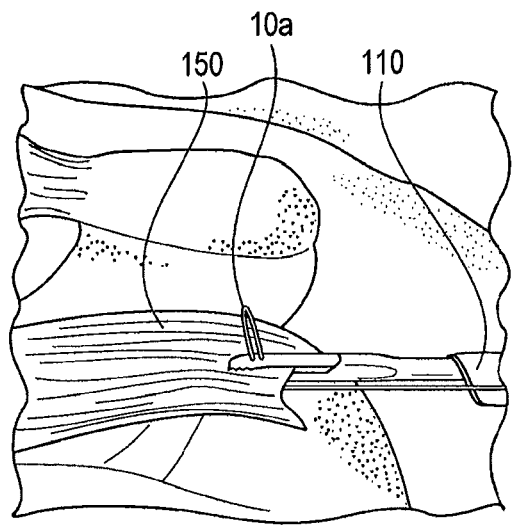

As shown in FIG. 2, the non-linked, free end 10a of a suture chain 10, such as the Arthrex FiberChain, is passed through the rotator cuff 150 using a suture passer 110, such as the Arthrex Scorpion™ Suture Passer, through a cannula, such as an Arthrex 5.75 mm Crystal Cannula. Next, the suture is retrieved through the same cannula.

Figure 3:
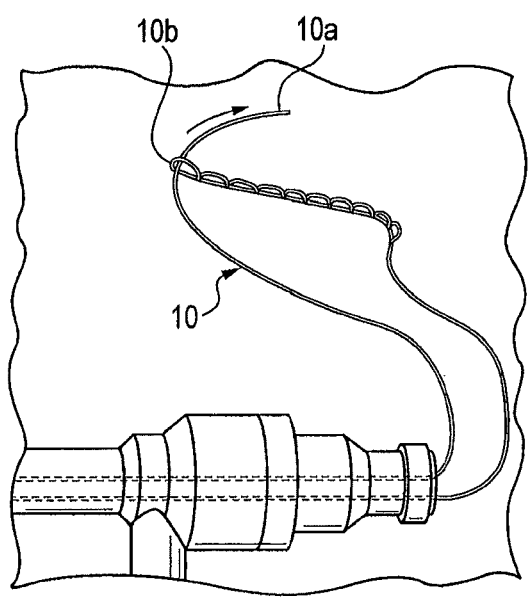

Then the free end 10a of suture chain 10 is passed through the terminal link 10b at its opposite end, as shown in FIG. 3. The loop 10b is cinched down by pulling on the free end 10a of the suture chain 10. The tip of the cannula may be used to help seat the suture chain loop securely against the rotator cuff 150. A suture retriever/tissue grasper 105 may be useful to ensure that the loop has been fully tightened. The, the second suture chain 11 is passed through the rotator cuff 150, the free end passed through the terminal loop, and the loop cinched in the same manner as for the first suture chain 10.

Figure 4:
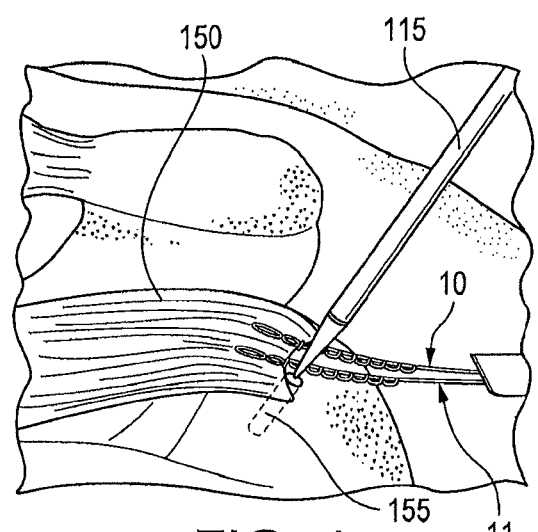

As shown in FIG. 4, the suture chain 10, 11 is used as a traction suture to determine the desired anchor location adjacent to the rotator cuff margin and a bone socket 155 is punched through a superolateral percutaneous portal with a punch 115, such as the Arthrex 5.5 mm Bio-Corkscrew FT Punch. A second bone socket 155 is also formed in the same manner for the second fiber chain 11.

Figure 5:
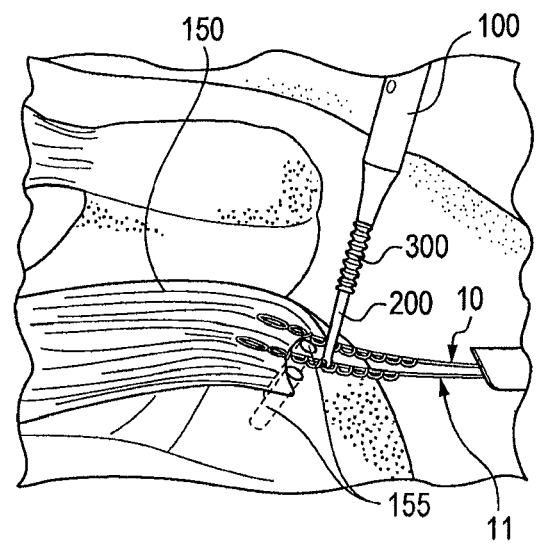

As shown in FIG. 5, both suture chain ends 10a, 11a are retrieved through the lateral portal. The swivel anchor 200 of the present invention is introduced through the percutaneous superolateral portal and captures the third link 10c from the free margin of the rotator cuff 150. The link 10c is captured by the forked anchor tip 250 of the anchor 200 (see FIG. 21). In a preferred embodiment, each link in the suture chain 10 is approximately 6 mm in length; therefore, since the total length of the swivel anchor 200 is 18 mm, capturing the third link 10c from the cuff edge will usually position the cuff directly at the edge of the bone socket 155 and perfectly tension the suture chain 10 and the rotator cuff 150 segment that it spans, when the anchor tip 250 pushes the suture chain 10 to the bottom of the bone socket 155.

Figure 6:
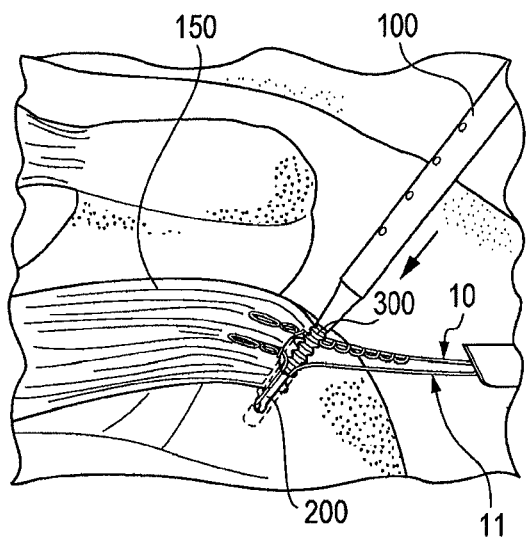
Figure 6A:
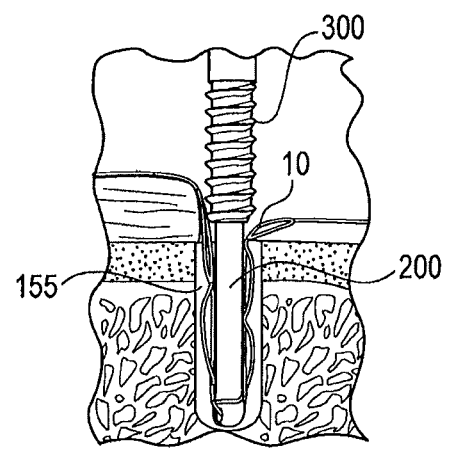

The tissue tension is then evaluated, as shown in FIGS. 6 and 6a. The driver assembly 100 is advanced into the bone socket 155 and the suture chain 10 is pushed toward the bottom of the socket 155 until the anchor body 225 contacts the bone. If the tension is not adequate, the driver 100 is removed from the bone socket 155 by pulling on the free end of the suture chain 10 (to release any wedging of the swivel-tip 250) at the same time that the driver assembly 100 is withdrawn. Then the adjacent, more proximal link is instead captured. If the tension is too great to fully insert the driver 100 to the bottom of the bone socket 155, the driver 100 is removed and the adjacent, more distal link is captured. Then the driver 100 is reinserted to the base of the bone socket. The forked tip 250 of the implant 200 is held to the driver with a zero retention suture cleated at the driver's proximal end.

Figure 7:
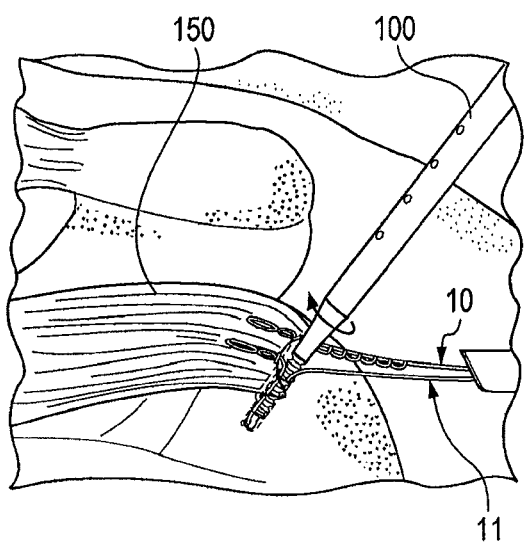
Figure 7A:
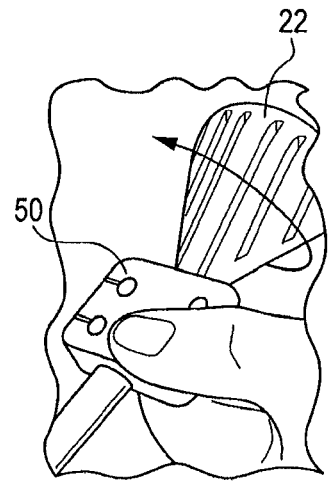

Fixation device 300, such as a screw, is advanced by driver assembly 100 by holding the thumb pad 50 as the inserter handle 22 is turned clockwise, as shown in FIGS. 7 and 7a. When the implant 400 is fully seated, the shaft 225 of the anchor 200 is fully engaged by the fixation device 300 to optimize the stability of the swivel anchor construct 400. The swivel anchor construct 400 comprises anchor 200 and fixation device 300. The tip retention suture is unwound from the cleat at the back of the driver handle 22 and the driver assembly 100 is removed. Then, one limb of the retention suture is pulled to fully remove it from the implant.

Figure 8:
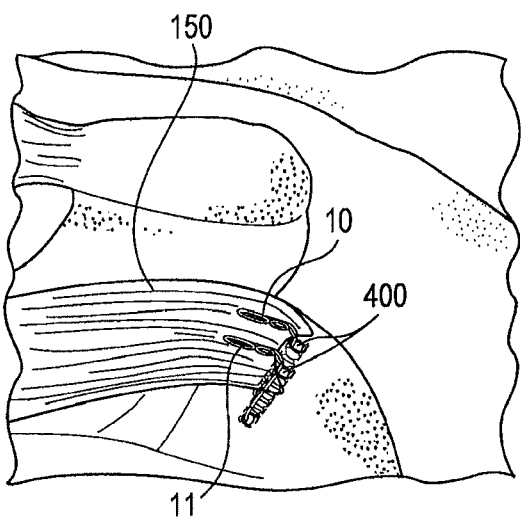
Figure 8A:
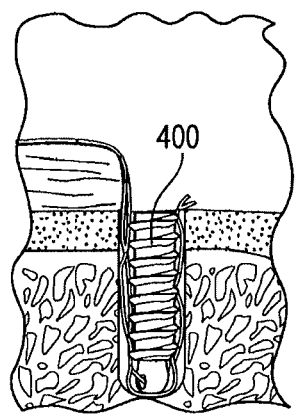

The insertion steps are repeated for the second swivel anchor construct 400 to obtain the final suture/anchor construct, shown in FIGS. 8 and 8a. The free suture ends 10a, 11a are cut with a suture cutter, such as the Arthrex open ended FiberWire Suture Cutter, so that they are flush with the edge of the bone socket 155.

Knotless Double Row Repair Technique—FIGS. 9-16 and 16a

FIGS. 9-16 and 16a illustrate a series of subsequent steps in shoulder repair for a double-row repair technique using a swivel anchor according to the present invention.

The mobility of the tear is assessed using suture retriever/tissue grasper. In the case of a large U-shaped tear, margin convergence suturing may be required before approximation of the tendon. A shaver, high-speed burr, or chondro pick is used to prepare a bleeding bone bed. Then, as shown in FIG. 9, pilot holes 160 are prepared for two suture anchors 120, such as Arthrex Bio-Corkscrew FT suture anchors, that will comprise the medial row through a percutaneous superolateral portal. A punch 115, such as the Arthrex 5.5 mm Bio-Corkscrew FT Punch, is advanced to the laser line at a 45° "deadman" angle, adjacent to the articular margin of the humerus to form the pilot holes 160. Tapping is seldom, but may be, necessary.

As shown in FIGS. 10 and 10a, both suture anchors 120 are placed. In a preferred embodiment, the suture anchors 120 come preloaded with suture chain 10.

Figure 11:
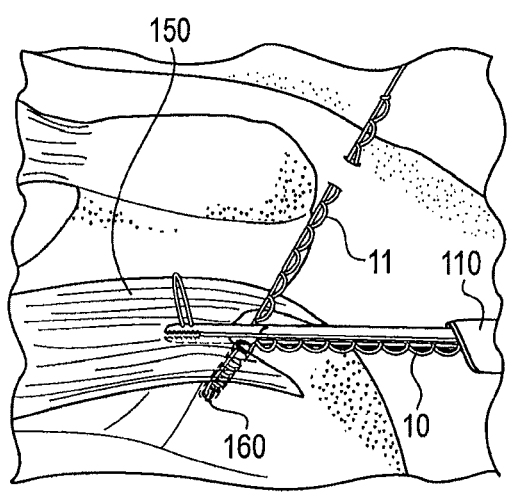

Then, as shown in FIG. 11, the suture leader is retrieved from one of the suture chain 10 strands through the lateral portal and is loaded onto a suture passer 110, such as the Arthrex Scorpion Suture Passer. The suture chain 10 suture leader is passed through the rotator cuff 150 approximately 15 mm from the free margin of the rotator cuff 150. This step is then repeated for the second suture chain 11.

Figure 12:
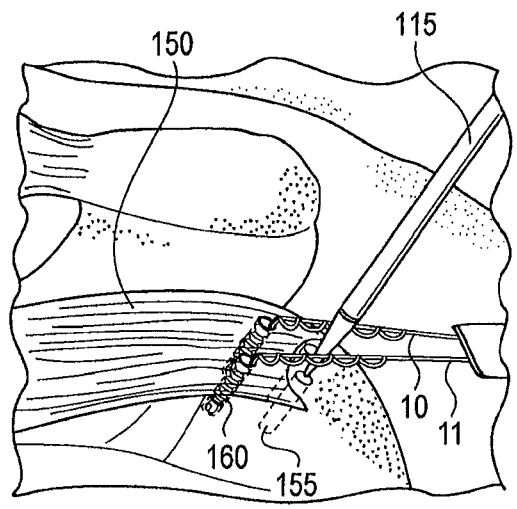

As shown in FIG. 12, both suture chain suture ends 10a, 11a are retrieved through the lateral portal and are tensioned to bring the cuff into contact with the medial portion of the footprint. The tip of the cannula may be used to push the tendon against the footprint. Then two bone sockets 155 are formed for the lateral row swivel anchors 200 using a punch 115. These two bone sockets 155 should be adjacent to the lateral margin of the cuff 150 when the cuff 150 is appropriately tensioned by the two previously placed suture chains 10, 11.

Figure 13:
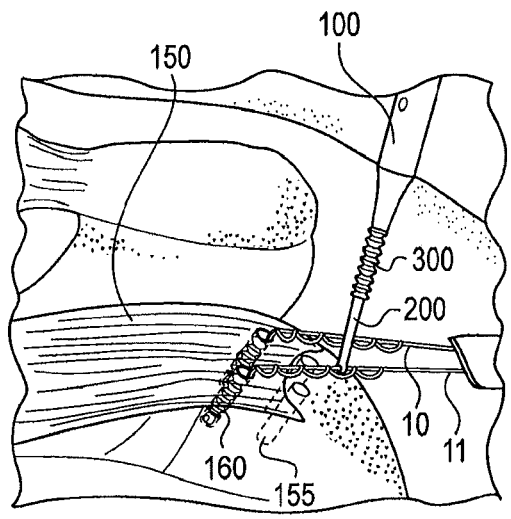

As shown in FIG. 13, the swivel anchor 200 is introduced through the percutaneous superolateral portal, capturing the third link 10c from the free margin of the rotator cuff 150. The link 10c is captured by the forked anchor tip 250 of the anchor 200 (see FIG. 21). In a preferred embodiment, each link in the suture chain 10, 11 is approximately 6 mm in length; therefore, since the total length of the swivel anchor 200 is 18 mm, capturing the third link from the cuff edge will usually position the cuff directly at the edge of the bone socket 155 and perfectly tension the suture chain 10 and the rotator cuff segment that it spans when the anchor tip 250 pushes the suture chain 10 to the bottom of the bone socket 155.

Figure 14:
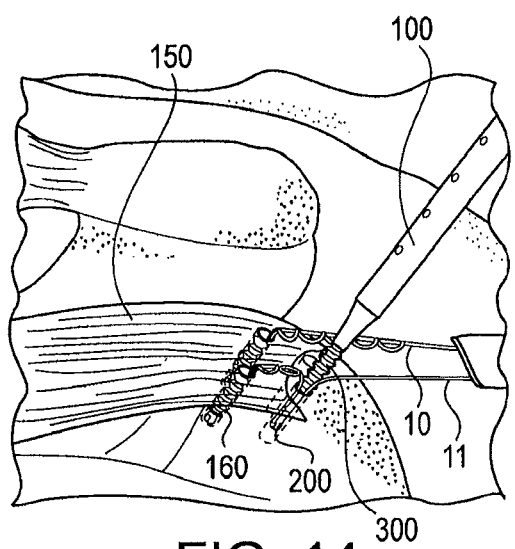

The tissue tension is then evaluated, as shown in FIG. 14. The driver assembly 100 is advanced into the bone socket 155 and the suture chain 10 is pushed toward the bottom of the socket 155 until the anchor body 225 contacts the bone. If the tension is not adequate, the driver is removed from the bone socket by pulling on the free end of the suture chain 10 (to release any wedging of the swivel-tip 250) at the same time that the driver assembly 100 is withdrawn and the adjacent, more proximal link is instead captured. If the tension is too great to fully insert the driver to the bottom of the bone socket 155, the driver assembly 100 is removed and the adjacent, more distal link is instead captured. Then the driver 100 is reinserted to the base of the bone socket 155.

Figure 15:
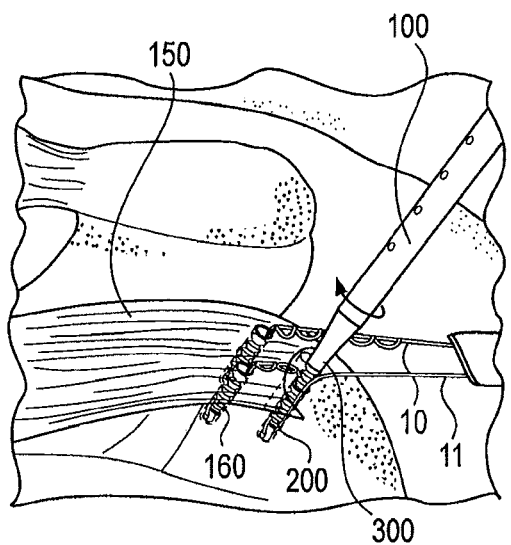
Figure 15A:
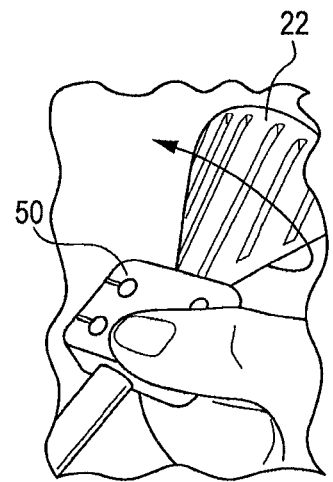

Fixation device 300, e.g., a screw, is advanced by holding the thumb pad 50 as the inserter handle 22 is turned clockwise, as shown in FIGS. 15 and 15a. When the implant 400 is fully seated, the shaft 225 of the anchor 200 is fully engaged by the body of the fixation device 300 to optimize the stability of the swivel anchor construct 400. As previously stated, the swivel anchor construct 400 comprises anchor 200 and fixation device 300. The tip retention suture is unwound from the cleat at the back of the driver handle 200 and the driver 100 is removed. One limb of the retention suture is pulled to fully remove it from the implant.

Figure 16:
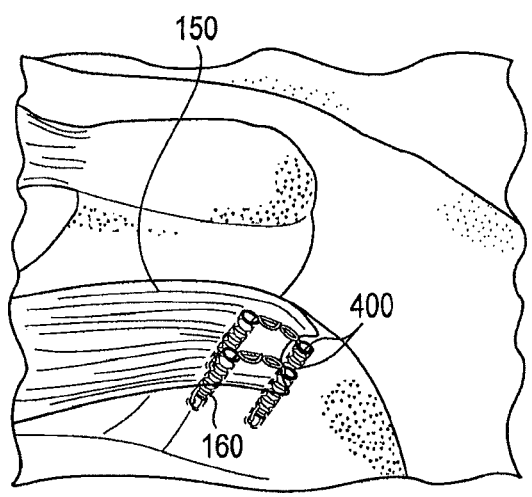
Figure 16A:
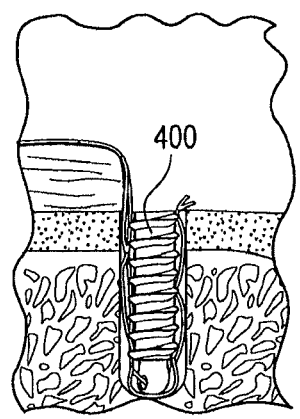

The steps of FIGS. 13-15 and 15a are then repeated for the second swivel anchor construct 400 to obtain the final construct, shown in FIGS. 16 and 16a. The free suture ends are cut with a suture cutter so that they are flush with the edge of the bone socket 155.

In addition to the above exemplary embodiments, the invention may also be used for a side-to-side closure of soft tissue using a suture chain 10. This method includes using the suture chain 10 to perform the side-to-side closure of the soft tissue with a final step of anchoring a chain link at the lateral aspect of the repair to bone using an anchor, such as anchor 200. The anchoring step is the same as that illustrated in the first two embodiments. Furthermore, if the soft tissue split to be repaired overlies bone for its entire length, a suture anchor, similar to suture anchor 120, may be inserted into bone at the medial aspect of the repair, a side-by-side margin convergence is implemented using the suture chain in a "shoelace-type" stitch, and the suture chain is anchored at the lateral aspect of the repair to bone using an anchor, such as anchor 200.

Figure 17A:
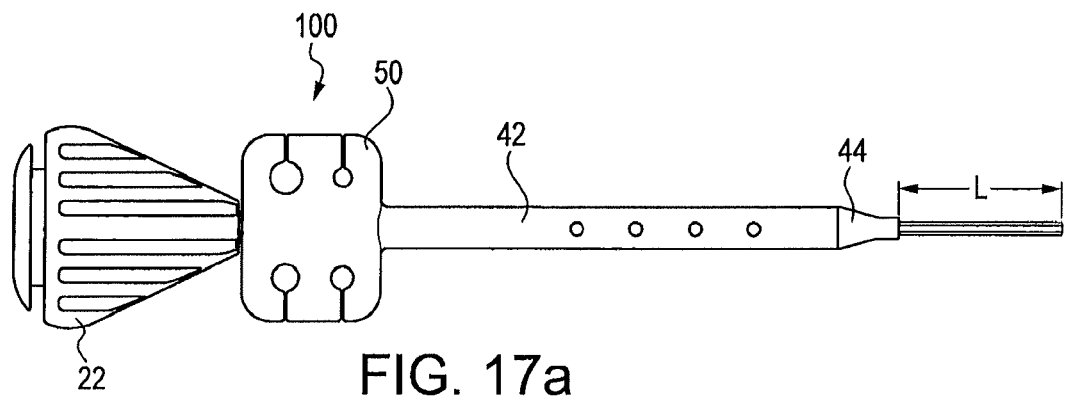
FIGS. 17a and 17b illustrate various views of a driver assembly comprising a rod, an inserter member, a threaded gauge and an end piece, according to the present invention.
Figure 17B:
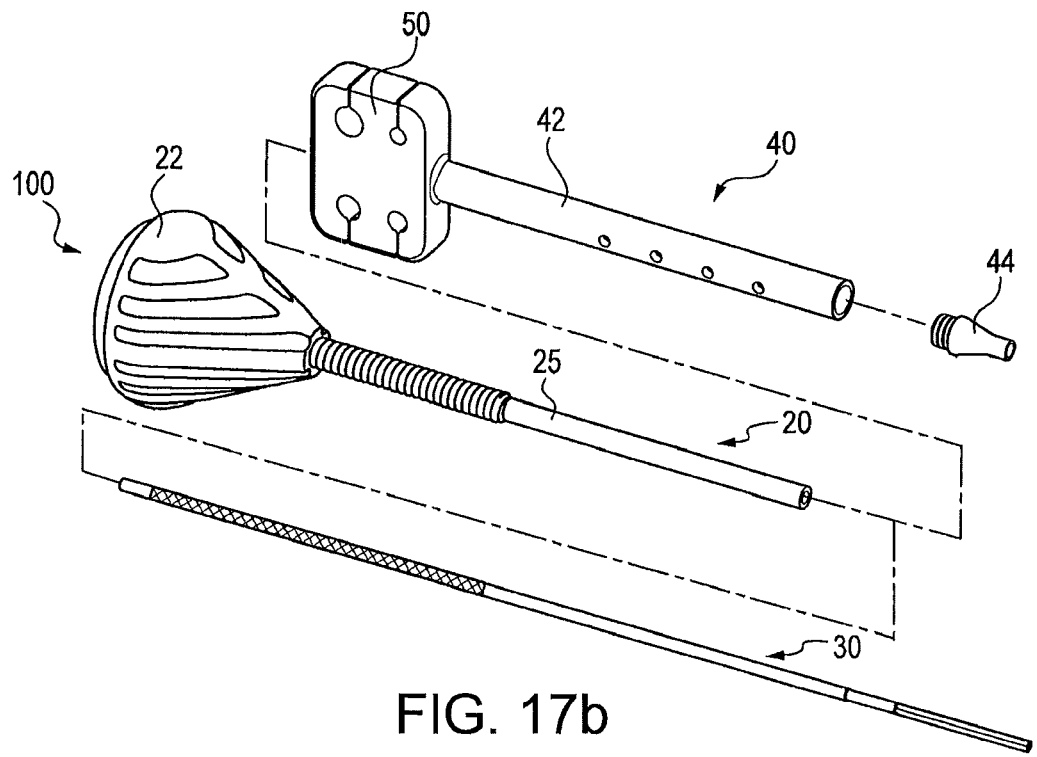
Figure 18:
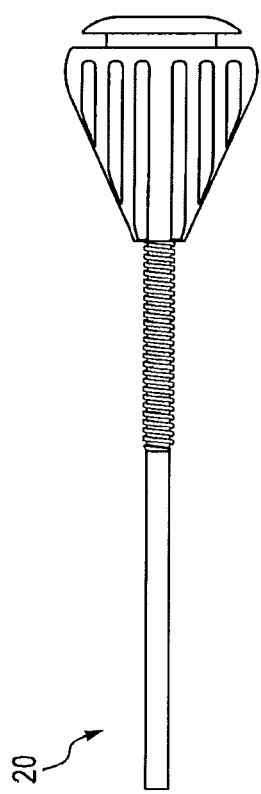
FIG. 18 illustrates various views of the inserter member of the driver assembly of FIGS. 17a and 17b.
Figure 19:
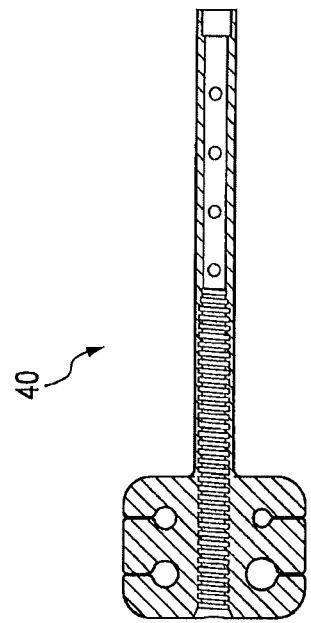
FIG. 19 illustrates various views of the threaded gauge with thumb pad of the driver assembly of FIGS. 17a and 17b.
Figure 20:
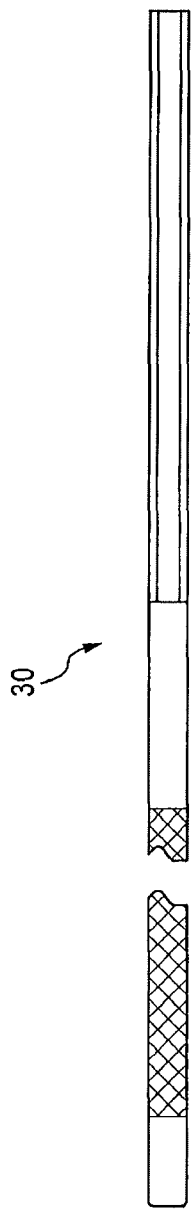
FIG. 20 illustrates various views of the rod of the driver assembly of FIGS. 17a and 17b.

Reference is now made to FIGS. 17a-22, which illustrate details of the driver assembly 100 (FIGS. 17a-20), the swivel suture anchor 200 (FIG. 21) and the fixation device 300 (FIG. 22). As illustrated in FIGS. 17a-20, driver assembly 100 comprises a cannulated driver 20 including shaft 25 and inserter handle 22; tube or rod 30 that passes slidably and rotatably through the cannulated driver 20; threaded gauge 40 including a cannulated body 42 and thumb pad 50; and tip 44. FIGS. 17a and 17b illustrate the driver assembly 100 both in assembled (a) and unassembled (b) form. FIG. 18 provides a more detailed view of the cannulated driver 20 of the driver assembly 100. FIG. 19 provides a more detailed view of the threaded gauge 40 of the driver assembly 100. FIG. 20 provides a more detailed view of the rod 30 of the driver assembly 100.

Figure 21:
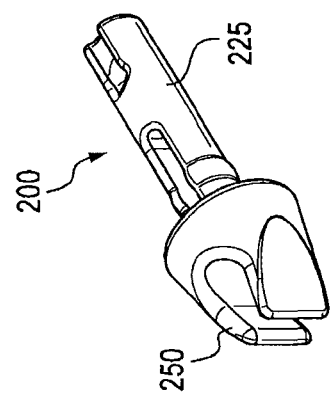
FIG. 21 illustrates various views of a swivel anchor according to the present invention.
Figure 22:
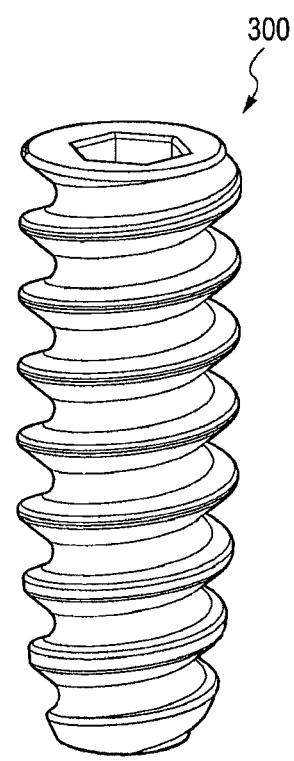
FIG. 22 illustrates various views of a fixation device according to the present invention and used in conjunction with the swivel anchor of FIG. 20 and the driver of FIG. 17.

FIG. 21 illustrates various views of swivel anchor 200. During installation of swivel anchor 200, the anchor body 225 is assembled onto the operational end of the driver 100. The anchor tip 250 is threaded or otherwise attached onto the tip of thin rod or tube 30. As detailed above, forked anchor tip 250 is used to capture a suture chain 10, 11 (that has been laced through a shoulder ligament, as shown in the two exemplary embodiments above) for installation into a pre-drilled hole 155 in bone. The suture anchor 200 has a threaded body 225 and a detachable forked tip 250. The forked tip 250 may be rotatably attached to the anchor body 225. This enables rotational insertion of the suture anchor 200 without causing excessive twisting and knotting of the suture chain 10, 11 by the forked tip 250.

FIG. 22 illustrates various views of a fixation device 300 (for example, a cannulated interference screw) that is employed in conjunction with the driver assembly 100 and the swivel anchor 200. Preferably, the fixation device 300 is preloaded on the driver assembly 100. As described above with reference to the two exemplary embodiments, the fixation device 300 is advanced into the bone socket 155 by holding the thumb pad 50 as the inserter handle 22 is turned clockwise. When the fixation device 300 is fully seated, the shaft 225 of the forked swivel anchor 200 is fully engaged by the fixation device 300 to optimize the stability of the swivel anchor construct 400. As previously stated, the swivel anchor construct 400 is composed of anchor 200 and fixation device 300.

In the two exemplary embodiments detailed above, suture anchor 200 is an Arthrex Swivel-Lock™ (swivel suture anchor). However, suture anchor 200 may be also a bone anchor or an Arthrex Push-Lock™-type anchor including a forked tip in order to capture a given link of the suture chain. Alternatively, the suture chain 10, 11 passed through the tissue can be secured either using a single anchor or a plurality of anchors. In addition, various anchors, such as those noted above and others, may be used interchangeably with only slight variations in the above procedure. For example, the suture chain 10, 11 can be secured by capturing two of the chain loops in forked tines prior to insertion of the anchor or anchors.

Further, regular suture may be used in addition to the suture chains of the present invention. In this case, the first suture anchor 120 of the double row embodiment will be pre-loaded with regular suture (for example, the Arthrex BioCorkscrew™ or Arthrex BioCorkscrew-FT™, disclosed in U.S. Application Publication No. 2007/0060922). In an exemplary embodiment using regular suture, the technique is similar to the one described above, except that the lateral fixation is accomplished by capturing the suture limbs (rather than chain-links) in the fork of the anchor 200 and tensioning the suture as the anchor 200 is placed. This relies on interference fixation of the suture between the anchor 200 and the bone.

As described above, the swivel anchor and suture chain assembly of the present invention has application in surgical tissue repair, for example, in conjunction with one or more bone anchors. Tension on repair constructs is adjustable through selection of the chain link or links to be snagged by a bone anchor.

Although the present invention has been described in relation to particular embodiments thereof, many other variations and modifications and other uses will become apparent to those skilled in the art. It is preferred, therefore, that the present invention be limited not by the specific disclosure herein.

What is claimed as new and desired to be protected by Letters Patent of the United States is:

1. A method of tissue fixation comprising:
   securing a suture to tissue to be fixated; and
   anchoring the suture in a bone socket using a swivel anchor mounted onto a tip of a driver, the driver being preloaded with a cannulated fixation device, the swivel anchor including a tip and a shaft, the suture being anchored in the bone socket by capturing the suture with the tip of the swivel anchor, advancing the swivel anchor with the captured suture into the bone socket, subsequently inserting the cannulated fixation device into the bone socket behind the swivel anchor by holding a thumb pad of the driver and turning a handle of the driver and rotating the driver to rotate and advance the cannulated fixation device so that the cannulated fixation device advances over the shaft of the swivel anchor and fully engages the shaft of the swivel anchor to optimize the stability of the swivel anchor, the cannulated fixation device being rotatable relative to the swivel anchor to enable rotational insertion of the cannulated fixation device over the shaft of the swivel anchor.

2. The method of claim 1, wherein the step of securing the suture to the tissue comprises passing the suture through the tissue.

3. The method of claim 2, further comprising the step of tensioning the tissue by pulling the captured suture before inserting the cannulated fixation device into the bone socket.

* * * * *